United States Patent [19]

Poepel et al.

[11] Patent Number: 5,559,066
[45] Date of Patent: Sep. 24, 1996

[54] PREPARATION OF IRON-, POTASSIUM- AND CERIUM-CONTAINING CATALYSTS

[75] Inventors: Wolfgang J. Poepel, Darmstadt; Gregor Tremmel, Gruenstadt; Wolfgang Buechele, Ludwigshafen; Axel Deimling, Neustadt; Hermann Petersen, Gruenstadt, all of Germany

[73] Assignee: BASF Aktiengesellschaft, Ludwigshafen, Germany

[21] Appl. No.: 381,916

[22] PCT Filed: Nov. 5, 1993

[86] PCT No.: PCT/EP93/03083

§ 371 Date: Feb. 13, 1995

§ 102(e) Date: Feb. 13, 1995

[87] PCT Pub. No.: WO94/11104

PCT Pub. Date: May 26, 1994

[30] Foreign Application Priority Data

Nov. 9, 1992 [DE] Germany .......................... 42 37 740.4

[51] Int. Cl.⁶ .................................................. B01J 38/00
[52] U.S. Cl. .............................................. 502/20; 585/661
[58] Field of Search ............................... 502/20; 585/661

[56] References Cited

U.S. PATENT DOCUMENTS

| | | |
|---|---|---|
| 2,666,086 | 1/1954 | Pitzer . |
| 2,831,041 | 4/1958 | Steg et al. . |
| 4,888,316 | 12/1989 | Gardner et al. ............ 502/20 |
| 4,975,399 | 12/1990 | Gardner .................... 502/38 |
| 5,324,695 | 6/1994 | Karrer et al. ............... 502/28 |

FOREIGN PATENT DOCUMENTS

| | | |
|---|---|---|
| 0195252 | 8/1986 | Germany . |
| 4237740 | 5/1994 | Germany . |

*Primary Examiner*—Anthony McFarlane
*Attorney, Agent, or Firm*—Keil & Weinkauf

[57] ABSTRACT

A process for the preparation of iron-, potassium- and cerium-containing catalysts for the dehydrogenation of hydrocarbons from the same spent catalysts (regeneration) by grinding and, if necessary, purifying the spent material, restoring the original activity by adjusting the composition and restoring the external shape comprises adding to the ground material an effective amount of potassium and such an amount of cerium that the total amount of cerium is greater than the amount originally present.

3 Claims, No Drawings

PREPARATION OF IRON-, POTASSIUM- AND CERIUM-CONTAINING CATALYSTS

The regeneration of datalysts is a very old aim in catalyst research, since spent catalysts are generally a valuable source of the elements present in them, or compounds thereof. For environmental protection reasons, disposable to landfill, i.e. avoidance of regeneration, is no longer acceptable, even in cases where they comprise inexpensive constituents such as iron oxide or aluminum oxide.

There have therefore already been many proposals, some very old, for recovery or reprocessing of the catalyst material.

In principle, a distinction is made between shape-retaining and re-shaping regeneration. While in the first case only impurities (for example carbon black and the like) are removed (cf. U.S. Pat. No. 2,831,041 (1954)) and any missing constituents are replaced, for example by impregnation with an appropriate solution of the constituent, reshaping is frequently preferred, in particular in the case of unsupported catalysts, which have a long life per se.

This was originally (cf. U.S. Pat. No. 2,666,086 (1949)) carried out, in the case of dehydrogenation catalysts, which traditionally essentially comprise iron oxide, by dissolving the entire catalyst in an acid, re-establishing the composition, and then precipitating or evaporating the solution in the conventional manner and reshaping the desired catalyst from the resultant solid.

However, it is desirable to avoid the chemical recreation of the active constituents (is. dissolution and reprecipitation).

It is an object of the present invention to provide a process for the preparation of iron-, potassium- and cerium-containing catalysts (cf. EP 195 252, German Patent 28 15 874) for the dehydrogenation of hydrocarbons from the same spent catalysts (regeneration) by comminuting, for example by grinding, and, if necessary, purifying the spent material, restoring the original activity by adjusting the composition, and restoring the external shape, using a novel catalyst without the need for a chemical reaction. It has been found that the restoration of the original composition in the specific case of cerium-containing catalysts is not sufficient to restore the original activity.

We have found that this object is achieved by a process of the above type which essentially comprises adding to the comminuted, e.g. ground, material an effective amount of potassium and such an amount of cerium that the total amount of cerium is greater than the amount originally present.

It is naturally also possible for other constituents conventionally used in Fe/K/Ce catalysts to be restored to their original content or to another desirable content. Catalysts of this type are described in the aforementioned publications (EP and German patent), to which reference is made herein.

The invention is based on the surprising finding (which is not intended to restrict the invention) that specifically cerium is in no way completely extracted, i.e. disappears, from the catalysts according to the invention, but instead is converted into a form which cannot be regenerated by comminuting, e.g. grinding, alone.

The analytical composition must therefore be corrected with respect to the cerium content; whereas fresh catalysts contain from about 5 to 40 (in particular 5 to 20) % by weight of potassium, from 0.1 to 20 (in particular 1 to 20) % by weight of cerium and possibly further constituents in addition to a predominant amount (for example from 40 to 90% by weight, in particular from 70 to 90% by weight) of iron oxide ($Fe_2O_3$), the total amount of the catalyst constituents being 100% by weight, a regenerated catalyst should now contain from 2 to 40% by weight of cerium in addition to the other constituents, which are present in correspondingly smaller amounts. Further regeneration, i.e. repetition of the regeneration of a catalyst which has already been regenerated one or more times, is possible, the cerium content increasing further in purely analytical terms. This is unimportant for the activity since it is known that even catalysts which comprise predominantly cerium oxide, i.e. from the outset, can readily be used for dehydrogenation. It goes without saying that a catalyst which has been regenerated a number of times in accordance with the invention can ultimately still be recycled by dissolution, recovery of the elements present therein and re-preparation, in which case the original composition can, if desired, be restored. It also goes without saying that a regenerated catalyst can be supplemented by fresh catalyst, for example if a larger amount than originally present is needed.

EXAMPLES

The performance of a dehydrogenation catalyst is assessed firstly using the selectivity and secondly using the activity.

The selectivity is the ability of the catalyst to promote the desired reaction and to suppress or not promote undesired reactions. In the case of the conversion of ethylbenzene into styrene, it is determined by measuring the ratio between the weight of styrene produced and the weight of ethylbenzene reacted and is given in mol percent (also known elsewhere as yield, but this can cause confusion since the conversion, i.e. the conversion per pass, is frequently also referred to as yield).

The activity is the performance of the catalyst measured by the reaction temperature. It is—under comparable conditions—measured and given as the temperature at which a certain conversion (per pass) is achieved; in the present case, the conversion of ethylbenzene is set at 70 mol %. This arises from the fact that the reaction temperature (temperature of a heat source surrounding the reactor, such as electrical heating or a salt bath) is varied. It thus goes without saying that a higher activity is indicated by a lower reaction temperature and vice versa.

In practice, in each case 1,000 g of catalyst were introduced into a steel tube 30 mm in width and 1,200 mm in length, around which a heatable and adjustable electrical heating source was coiled and which was provided with conventional fittings for the inlet and outlet of the gas mixture and for carrying out long-term experiments. The experiment duration was in each case 3 weeks; the weights produced and used within half an hour were then determined and the activity and selectivity calculated (cf. Table 2).

Novel catalyst

A catalyst of the composition shown in Table 1 (cf. EP 195 252) was investigated in the virtually fresh state.

EXPERIMENT 1 (comparison)

The catalyst of the composition shown in Table 1 was used for about one year in a plant under usual industrial conditions, removed and investigated as described above (composition cf. Table 1).

EXPERIMENT 2 (comparison)

The catalyst material used (cf. Experiment 1) was brought to the original composition of the novel catalyst and investigated.

EXAMPLE 1 (according to the invention)

The catalyst material used (cf. Experiment 1) was first heated to 800° C. in order to remove deposits and to improve grindability, finely ground, adjusted to the composition shown in Table 1 and again shaped to give pellets.

TABLE 1

Chemical composition* of the catalysts [% by weight]

|  | $Fe_2O_3$ | $K_2O$ | $WO_3$ | $Ce_2O_3$ | CaO |
|---|---|---|---|---|---|
| Novel catalyst | 77.0 | 12.3 | 3.9 | 4.9 | 1.9 |
| Experiment 1 | 79.7 | 10.1 | 3.7 | 4.6 | 1.9 |
| Experiment 2 | 77.0 | 12.3 | 3.9 | 4.9 | 1.9 |
| Example 1 | 75.5 | 11.2 | 3.7 | 7.6 | 2.0 |

*The catalyst constituents in each case total 100%

TABLE 2

Properties of the catalysts
(3 mm pellets – conversion = 70 mol %)

|  | Selectivity (%) | Activity (°C.) |
|---|---|---|
| Novel catalyst | 94.7 | 615 |
| Experiment 1 | 94.0 | 625 |
| Experiment 2 | 94.1 | 622 |
| Example 1 | 94.9 | 615 |

We claim:

1. A process for regenerating spent iron-, potassium-, and cerium-containing catalysts for the dehydration of hydrocarbons which comprises: grinding the spent catalysts and adding to the ground material an effective amount of potassium and such an amount of cerium that the total amount of cerium is greater than the amount originally present.

2. The process as claimed is claim 1, wherein the catalyst is calcined before re-use.

3. The process as claimed in claim 1, wherein the spent catalyst is calcined in the presence of air or oxygen before the grinding.

* * * * *